(12) United States Patent
Igaue

(10) Patent No.: US 11,241,331 B2
(45) Date of Patent: Feb. 8, 2022

(54) HEATING COMPRESS

(71) Applicant: KOBAYASHI PHARMACEUTICAL CO., LTD., Osaka (JP)

(72) Inventor: Tsuyoshi Igaue, Ibaraki (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/759,048

(22) PCT Filed: May 2, 2016

(86) PCT No.: PCT/JP2016/063610
§ 371 (c)(1),
(2) Date: Apr. 19, 2018

(87) PCT Pub. No.: WO2017/043119
PCT Pub. Date: Mar. 16, 2017

(65) Prior Publication Data
US 2019/0038458 A1 Feb. 7, 2019

(30) Foreign Application Priority Data

Sep. 11, 2015 (WO) .................. PCT/JP2015/075810
Sep. 11, 2015 (WO) .................. PCT/JP2015/075811

(51) Int. Cl.
*A61F 7/03* (2006.01)
*A61F 7/02* (2006.01)

(52) U.S. Cl.
CPC ................ *A61F 7/034* (2013.01); *A61F 7/03* (2013.01); *A61F 2007/022* (2013.01);
(Continued)

(58) Field of Classification Search
CPC ............. A61F 7/03; A61F 7/032; A61F 7/034
See application file for complete search history.

(56) References Cited

U.S. PATENT DOCUMENTS

2008/0202490 A1* 8/2008 Dodo ...................... A61F 7/034
126/263.07
2008/0257333 A1* 10/2008 Dodo ...................... A61F 7/034
126/263.09

(Continued)

FOREIGN PATENT DOCUMENTS

EP 2 581 065 A1 4/2013
JP H10-152432 A 6/1998
(Continued)

OTHER PUBLICATIONS

Machine Translation of JP 2002-177313A (Year: 2002).*
(Continued)

*Primary Examiner* — Kaitlyn E Smith
(74) *Attorney, Agent, or Firm* — Knobbe, Martens, Olson & Bear, LLP

(57) ABSTRACT

An object of the present invention is to provide a heat-generating device with which a warm sensation is persistently perceived, and which can effectively exert a heating effect. In a heat-generating device that is used by being attached to skin, (1) a packaging material constituting a skin attachment surface of a housing is formed of a laminated sheet in which at least a moisture absorption layer that absorbs moisture and a moisture barrier layer that blocks penetration of moisture are laminated in this order from the adhesive layer, (2) an adhesive layer is partially provided on a surface of the moisture absorption layer, and (3) a warming agent that allows an enhanced warm sensation to be perceived in the presence of moisture is contained in at least one of the adhesive layer and the moisture absorption layer. This heat-generating device thereby has improved persistence of a perceived warm sensation, and can exert a markedly high heating effect.

10 Claims, 3 Drawing Sheets

(52) U.S. Cl.
 CPC . *A61F 2007/026* (2013.01); *A61F 2007/0207* (2013.01); *A61F 2007/0226* (2013.01)

(56) References Cited

U.S. PATENT DOCUMENTS

| | | |
|---|---|---|
| 2013/0079581 A1 | 3/2013 | Agamaite et al. |
| 2015/0320589 A1 | 11/2015 | Nishioka et al. |

FOREIGN PATENT DOCUMENTS

| | | |
|---|---|---|
| JP | 2002-177313 A | 6/2002 |
| JP | 2014-008288 A | 1/2014 |
| WO | WO 2014/157726 A1 | 10/2014 |

OTHER PUBLICATIONS

International Search Report for PCT/JP2016/063610, dated Jul. 26, 2016 in 1 page.
Supplemental European Search Report in corresponding European Application No. EP 16 84 3985, dated Mar. 18, 2019.
European Office Action issued for Counterpart European Patent Application. No. 16843985.9 (dated Nov. 13, 2019).
Office Action for counterpart Japanese Patent Application No. 2017-538808 dated Jun. 2, 2020.

\* cited by examiner

HEATING COMPRESS

TECHNICAL FIELD

The present invention relates to a heat-generating device. More specifically, the present invention relates to a heat-generating device with which a warm sensation is persistently perceived, and which can effectively exert a heating effect.

BACKGROUND ART

Conventionally, heat-generating devices that use an exothermic composition that generates heat upon contact with air have been extensively used not only as warming devices for protection from the cold and the like, but also as therapeutic devices and the like for promoting blood circulation, relieving pain, and the like. Disposable body warmers, for example, which have excellent portability, and are inexpensive, are suitably used as warming devices, therapeutic devices, and the like. Moreover, conventionally, heat-generating devices each having an adhesive layer, which are designed to be readily fixable to skin, have also been extensively used.

Furthermore, heat-generating devices having adhesive layers containing active ingredients for imparting various functionalities to the heat-generating devices have been conventionally proposed. Patent Literature 1, for example, discloses a heat-generating device having an adhesive layer containing an active ingredient. Patent Literature 1 also discloses that a warming component can be used as an active ingredient contained in the adhesive layer. Such a heat-generating device including an adhesive layer containing a warming agent is expected to have an improved heating effect.

In recent years, there has been an increasing consumer demand for improved functionalities of heat-generating devices, and there is an urgent need for the development of a heat-generating device that has improved persistence of a perceived warm sensation, and can exert a heating effect more effectively.

CITATION LIST

Patent Literature 1: JP 2014-8288 A

SUMMARY OF INVENTION

Technical Problem

An object of the present invention is to provide a heat-generating device with which a warm sensation is persistently perceived, and which can effectively exert a heating effect.

Solution to Problem

The inventor of the present invention conducted extensive research to solve the aforementioned problem, and found that a heat-generating device that is used by being attached to skin, which comprises the following features (1) to (3), has improved persistence of a perceived warm sensation, and can exert a markedly high heating effect:

(1) A packaging material constituting a skin attachment surface of a housing is formed of a laminated sheet in which at least a moisture absorption layer that absorbs moisture and a moisture barrier layer that blocks penetration of moisture are laminated in this order from the adhesive layer;

(2) An adhesive layer is partially provided on a surface of the moisture absorption layer; and (3) A warming agent that allows an enhanced warm sensation to be perceived in the presence of moisture is contained in at least one of the adhesive layer and the moisture absorption layer.

The present invention has been completed by conducting further research based on the findings. In summary, the present invention provides aspects of invention as itemized below.

Item 1. A heat-generating device that is used by being attached to skin, comprising:

a heat-generating portion that generates heat to be delivered to skin;

a housing that contains the heat-generating portion, and has a skin attachment surface that is to be attached to the skin; and an adhesive layer provided on the skin attachment surface of the housing, wherein a packaging material constituting the skin attachment surface of the housing is formed of a laminated sheet in which at least a moisture absorption layer that absorbs moisture and a moisture barrier layer that blocks penetration of moisture are laminated in this order from the adhesive layer, the adhesive layer is partially provided on a surface of the moisture absorption layer, and a warming agent that allows an enhanced warm sensation to be perceived in the presence of moisture is contained in at least one of the adhesive layer and the moisture absorption layer.

Item 2. The heat-generating device according to item 1, wherein, on the surface of the moisture absorption layer, an area ratio of an adhesive layer formation region where the adhesive layer is formed relative to a moisture absorption layer exposure region where the moisture absorption layer is exposed is 100:5-2000.

Item 3. The heat-generating device according to item 1 or 2, wherein, on the surface of the moisture absorption layer, the moisture absorption layer exposure region where the moisture absorption layer is exposed communicates with an edge of the moisture absorption layer.

Item 4. The heat-generating device according to any one of items 1 to 3, wherein the packaging material constituting the skin attachment surface of the housing has a barrier function to block penetration of the warming agent.

Item 5. The heat-generating device according to item 4, wherein the moisture barrier layer contains a resin layer formed of polyethylene terephthalate, polyacrylonitrile, or an ethylene-vinyl alcohol copolymer; a vapor-deposited film; and/or a metal foil film.

Item 6. The heat-generating device according to any one of items 1 to 5, wherein the moisture absorption layer is a fibrous sheet.

Item 7. The heat-generating device according to any one of items 1 to 6, wherein the warming agent is contained in the adhesive layer.

Item 8. The heat-generating device according to any one of items 1 to 7, wherein the warming agent is at least one selected from the group consisting of capsaicin, nonanoic acid vanillylamide, sage, caffeine, tocopherol nicotinate, nicotinic acid benzyl ester, vanillyl ethyl ether, vanillyl propyl ether, vanillyl butyl ether, vanillyl pentyl ether, vanillyl hexyl ether, vanillyl butyl ether acetate, gingerol, *Capsicum annuum* extract, and ginger extract.

Item 9. The heat-generating device according to any one of items 1 to 8, wherein the heat-generating portion is an exothermic composition that generates heat upon contact with oxygen, and the housing is at least partially air-permeable.

Advantageous Effects of Invention

The heat-generating device of the present invention allows a user to persistently perceive a warm sensation imparted by the heat-generating portion and a warm sensation imparted by the warming agent. This persistence of the warm sensation depends on the unique structure of the heat-generating device of the present invention, and is believed to be achieved by repetition of (1) to (4): (1) sweat is produced from the skin due to the warm sensation imparted by the heat-generating portion; (2) the sweat is absorbed by the moisture absorption layer; (3) the warm sensation imparted by the warming agent is enhanced via the absorbed sweat; and (4) when the user becomes perceptually used to the warm sensation, the user predominantly perceives the warm sensation imparted by the heat-generating portion.

The heat-generating device of the present invention allows a user to persistently perceive a warm sensation imparted by the heat-generating portion and a warm sensation imparted by the warming agent, and thus, can be suitably used as therapeutic devices for promoting blood circulation, reducing stiff shoulders, relieving pain, and the like. Furthermore, the heat-generating device of the present invention can suppress stickiness due to sweat during use, and can prevent removal from the skin, and thus, can provide an excellent feel in use.

DESCRIPTION OF EMBODIMENTS

Figure 1:
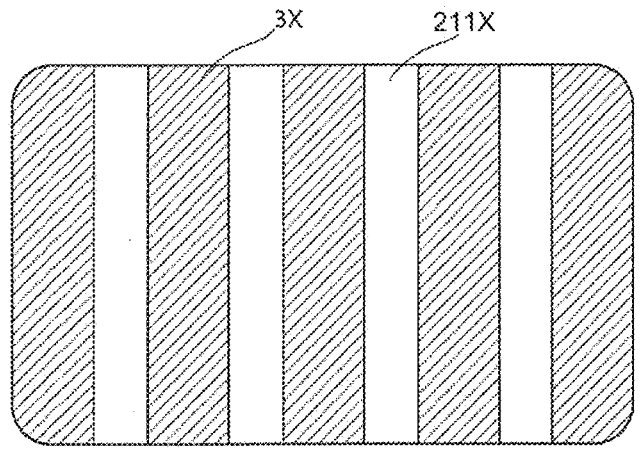
FIG. 1 is a schematic plan view of a heat-generating device in which an adhesive layer is provided in the form of stripes on a surface of a moisture absorption layer, as seen from the skin attachment surface.

The heat-generating device of the present invention is a heat-generating device that is used by being attached to skin, which comprises a heat-generating portion 1 that generates heat to be delivered to skin, a housing 2 that contains the heat-generating portion 1, and has a skin attachment surface that is to be attached to the skin, and an adhesive layer 3 provided on the skin attachment surface of the housing 2. Furthermore, in the heat-generating device of the present invention, a packaging material 21 constituting the skin attachment surface of the housing 2 is formed of a laminated sheet in which at least a moisture absorption layer 211 that absorbs moisture and a moisture barrier layer 212 that blocks penetration of moisture are laminated in this order from the adhesive layer 3, the adhesive layer 3 is partially provided on a surface of the moisture absorption layer 211, and a warming agent that allows an enhanced warm sensation to be perceived in the presence of moisture is contained in at least one of the adhesive layer 3 and the moisture absorption layer 211. The heat-generating device of the present invention will be hereinafter described in detail.

As used herein, the term "warm sensation" refers to a sensation concerning the warmth that is perceived when the heat-generating device is attached to the skin, and the term "heating effect" refers to physiological effects (such as promoting blood circulation, reducing stiff shoulders, and relieving pain) that are produced at the site of the skin where the heat-generating device is attached, by means of the physical generation of heat from the heat-generating device and the above-described warm sensation.

<Heat-Generating Portion 1>

The heat-generating device of the present invention comprises, as a heat-generating element, the heat-generating portion 1 that generates heat to be delivered to skin. The heat-generating portion 1 serves to generate heat, and impart a warm sensation.

The heat-generating portion 1 is not particularly limited in heat-generating mechanism so long as it can generate heat, and deliver it to the skin; examples of the heat-generating portion 1 include an exothermic composition that generates heat upon contact with oxygen; a current-carrying heat-generating element that generates heat by passage of current; a heat-generating element that generates heat when irradiated with microwaves; and a heat-generating element that generates heat using a liquid, semi-solid, or solid thermal storage material. Among the above, an exothermic composition that generates heat upon contact with oxygen, which is disposable, is suitably used as the heat-generating portion 1 in view of safety, heat-generation efficiency, convenience, and the like.

The composition of the exothermic composition that generates heat upon contact with oxygen is not particularly limited, and may be any composition that is conventionally used for disposable body warmers and the like. One suitable example of the exothermic composition that generates heat upon contact with oxygen is a composition containing an oxidizable metal, an oxidation promoter, and water.

In the exothermic composition, the oxidizable metal is oxidized by contact with oxygen, and serves as a heat-generating source by oxidative heat. While the oxidizable metal is not particularly limited in type so long as it can generate heat by oxidation, examples of oxidizable metals include metals such as iron (reduced iron, cast iron, atomized iron, and electrolytic iron), aluminum, zinc, manganese, magnesium, and calcium. These oxidizable metals may be used alone, or in combination of two or more.

While the oxidizable metal is not particularly limited in shape, the oxidizable metal is preferably in the form of a powder, particles, or fibers, and more preferably a powder, for example, from the viewpoint of heat-generation efficiency.

Among these oxidizable metals, an iron powder is preferred, for example, from the viewpoint of safety, handleability, and the like.

When the oxidizable metal is in the form of a powder, the particle diameter is, for example, 0.01 to 1000 μm, preferably 0.1 to 500 μm, more preferably 0.5 to 300 μm, and still more preferably 30 to 250 μm, although not particularly limited thereto. Herein, the particle diameter of the oxidizable metal in the form of a powder is a value measured in accordance with "dry sieving test" defined in JIS 8815-1994: "Test sieving—General requirements".

While the content of the oxidizable metal in the exothermic composition may be determined as appropriate in accordance with the heat-generating properties to be imparted, it is, for example, 20 to 80 wt %, preferably 25 to 70 wt %, and more preferably 30 to 60 wt %.

In the exothermic composition, the oxidation promoter serves to hold oxygen, and supplies oxygen to the oxidizable metal. While the oxidation promoter is not particularly limited in type so long as it can hold oxygen and supplies oxygen to the oxidizable metal, examples of oxidation promoters include carbon materials such as activated carbon, carbon black, acetylene black, bamboo charcoal, wood charcoal, coffee grounds charcoal, graphite, coal, coconut husk charcoal, bituminous coal, peat, and lignite. These oxidation promoters may be used alone, or in combination of two or more.

Among these oxidation promoters, activated carbon, carbon black, bamboo charcoal, wood charcoal, and coffee grounds charcoal are preferred, and activated carbon is more preferred, for example.

While the oxidation promoter is not particularly limited in shape, the oxidation promoter is preferably in the form of a powder, particles, or fibers, and more preferably a powder, for example, from the viewpoint of heat-generation efficiency.

When the oxidation promoter is in the form of a powder, the particle diameter is, for example, 0.001 to 1000 μm, preferably 0.005 to 500 μm, and more preferably 0.01 to 200 μm, although not particularly limited thereto. Herein, the particle diameter of the oxidation promoter in the form of a powder is a value measured in accordance with "dry sieving test" defined in JIS 8815-1994: "Test sieving—General requirements".

While the content of the oxidation promoter in the exothermic composition may be determined as appropriate in accordance with the heat-generating properties and the like to be imparted, it is, for example, 1 to 30 wt %, preferably 3 to 25 wt %, and more preferably 5 to 23 wt %.

Moreover, while the proportion of the oxidation promoter to the oxidizable metal in the exothermic composition may be determined as appropriate in accordance with the heat-generating properties to be imparted, the proportion of the oxidation promoter is, for example, 2 to 60 parts by weight, preferably 5 to 50 parts by weight, and more preferably 10 to 40 parts by weight, per 100 parts by weight of the oxidizable metal.

In the exothermic composition, water serves to oxidize the oxidizable metal together with oxygen. Any of distilled water, ion-exchange water, pure water, ultrapure water, tap water, industrial water, and the like may be used as water.

While the content of water in the exothermic composition may be determined as appropriate in accordance with the heat-generating properties to be imparted, it is, for example, 5 to 50 wt %, preferably 10 to 40 wt %, and more preferably 15 to 35 wt %.

The exothermic composition may contain a water-soluble salt, as required, in addition to the above-described components. When the exothermic composition contains a water-soluble salt, the water-soluble salt can promote oxidation of the oxidizable metal.

While the water-soluble salt is not particularly limited in type, examples of water-soluble salts include sulfates, hydrogen carbonates, chlorides, or hydroxides of alkali metals (such as sodium and potassium), alkaline earth metals (such as calcium and magnesium), or heavy metals (such as iron, copper, aluminum, zinc, nickel, silver, and barium). Among these water-soluble salts, chlorides such as sodium chloride, potassium chloride, calcium chloride, magnesium chloride, and iron(II, III) chloride are preferred, and sodium chloride is more preferred, for example, from the viewpoint of conductivity, chemical stability, and the like. These water-soluble salts may be used alone, or in combination of two or more.

When a water-soluble salt is contained in the exothermic composition, the content of the water-soluble salt may be determined as appropriate in accordance with the heat-generating properties to be imparted; for example, the content is 0.1 to 10 wt %, preferably 0.5 to 7 wt %, and more preferably 1 to 5 wt %.

The exothermic composition may also contain a water-retaining agent, as required. The water-retaining agent serves to hold water, and supplies water to the oxidation reaction field.

Examples of types of the water-retaining agent include, although not particularly limited to, inorganic porous materials such as vermiculite, perlite, calcium silicate, magnesium silicate, kaolin, talc, smectite, mica, bentonite, calcium carbonate, silica gel, alumina, zeolite, silicon dioxide, and diatomaceous earth; organic materials such as pulp, wood flour (sawdust), cotton, starches, and celluloses; and water-absorbing resins such as polyacrylic acid-based resins, polysulfonic acid-based resins, maleic anhydride-based resins, polyacrylamide-based resins, polyvinyl alcohol-based resins, polyethylene oxide-based resins, polyaspartic acid-based resins, polyglutamic acid-based resins, and polyalginic acid-based resins. These water-retaining agents may be used alone, or in combination of two or more.

Among these water-retaining agents, vermiculite, polyacrylic acid-based resins, wood flour, and pulp are preferred; and vermiculite and polyacrylic acid-based resins are more preferred, for example. When an inorganic porous material is used as the water-retaining agent, it can ensure a path through which air flows in the exothermic composition.

The particle diameter of the water-retaining agent is, for example, 0.1 to 3000 μm, preferably 0.5 to 1000 μm, and more preferably 1 to 1000 μm, although not particularly limited thereto. Herein, the particle diameter of the water-retaining agent is a value measured in accordance with "dry sieving test" defined in JIS 8815-1994: "Test sieving—General requirements".

When the water-retaining agent is contained in the exothermic composition, the content of the water-retaining agent may be determined as appropriate in accordance with the heat-generating properties to be imparted; for example, the content is 1 to 20 wt %, preferably 3 to 15 wt %, and more preferably 5 to 10 wt %.

The exothermic composition may also contain other additives such as a metal-ion sequestering agent, a fragrance, a thickener, an excipient, a surfactant, and a hydrogen generation inhibitor, as required.

The exothermic composition may be prepared by mixing predetermined amounts of the above-described components. While the exothermic composition may be prepared in the presence of oxygen, it is preferably prepared under reduced pressure or an inert gas atmosphere.

The heat-generating portion 1 is designed to generate heat at an appropriate temperature when the heat-generating device of the present invention is attached to the skin. The maximum reached temperature of the heat-generating device of the present invention may be determined as appropriate in accordance with the skin site to which the heat-generating device is to be applied, the warm sensation or heating effect to be imparted, and the like; for example, the maximum reached temperature is about 32 to 85° C., and preferably about 34 to 70° C. The maximum reached temperature is a value measured in accordance with the method defined in JIS S4100: 2007.

<Housing 2>

The heat-generating device of the present invention comprises the housing 2 that contains the heat-generating portion 1. The housing 2 has a housing portion 22 to contain the heat-generating portion 1.

The packaging material 21 disposed on the skin attachment surface (hereinafter sometimes referred to as the "skin attachment surface-side packaging material") of the housing 2 is formed of a laminated sheet in which at least the moisture absorption layer 211 that absorbs moisture and the moisture barrier layer 212 that blocks penetration of moisture are laminated in this order from the adhesive layer 3. In the skin attachment surface-side packaging material, the moisture barrier layer 212, which is laminated over the entire surface of the moisture absorption layer 211, is configured to block sweat absorbed by the moisture absorption layer 211 from penetrating inside the housing portion 22 or opposite to the skin attachment surface of the housing 2.

In the skin attachment surface-side packaging material 21, the moisture absorption layer 211 serves to absorb sweat due to the warm sensation through the portions not having the adhesive layer 3 (moisture absorption layer exposure region) to enhance the warm sensation imparted by the warming agent, thereby improving the persistence of the warm sensation. The moisture absorption layer 211 also serves to absorb sweat through the portions not having the adhesive layer 3 (moisture absorption layer exposure region), thereby suppressing stickiness due to sweat during use, and providing an excellent feel in use.

While the material constituting the moisture absorption layer 211 is not particularly limited so long as it has water-absorbing properties, examples of materials include fibrous materials, water-absorbing resin materials, and sponge-like resin materials. The moisture absorption layer 211 can be formed using, for example, a method that involves bonding a sheet formed of any of these materials to the moisture barrier layer 212; or a method that involves applying or loading any of these materials onto or into the moisture barrier layer 212 to form the moisture absorption layer. A fibrous sheet is preferred as a preferred form of the moisture absorption layer 211, from the viewpoint of the feel in use, adhesion to the adhesive layer 3, and the like.

Specific examples of fibrous sheets used as the moisture absorption layer 211 include nonwoven fabrics and woven fabrics. The fibrous sheet is preferably a nonwoven fabric, for example, from the viewpoint of the feel in use. Examples of fibers constituting the fibrous sheet include, although not particularly limited to, synthetic fibers such as polyethylene terephthalate, polybutylene terephthalate, nylon, polypropylene, polyethylene, vinylon, rayon, acrylic, acetate, and polyvinyl chloride; natural fibers such as cotton, hemp, silk, and paper; and mixtures of these fibers. Among these fibers, polyethylene terephthalate, nylon, and polypropylene are preferred, and polyethylene terephthalate and nylon are more preferred, for example, from the viewpoint of enhancing the feel in use.

The fibrous sheet used as the moisture absorption layer 211 may also be loaded with a water-absorbing resin (including a superabsorbent resin (SAP)), as required, to enhance the water absorbency.

The weight per unit area of the fibrous sheet used as the moisture absorption layer 211 is, for example, 10 to 100 $g/m^2$, preferably 15 to 70 $g/m^2$, and more preferably 20 to 50 $g/m^2$, although not particularly limited thereto.

In the skin attachment surface-side packaging material 21, the moisture barrier layer 212 serves to prevent sweat from penetrating inside the housing 2 or to the outside opposite to the skin attachment surface of the housing 2, from the moisture absorption layer 211 that has absorbed the sweat, thereby preventing a decrease in the persistence of the warm sensation.

While the material constituting the moisture barrier layer 212 is not particularly limited, examples of materials include a resin layer formed of a thermoplastic resin, a vapor-deposited film, and a metal foil film. The moisture barrier layer 212 may have a single layer structure composed of one layer only, or may have a multilayer structure composed of two or more layers formed of the same or different materials. From the viewpoint of the ease of manufacture and the like of the housing 2, at least one layer constituting the moisture barrier layer 212 is preferably a resin layer formed of a thermoplastic resin.

Specific examples of thermoplastic resins forming the resin layer used as the moisture barrier layer 212 include polyethylene terephthalate, polyacrylonitrile, ethylene-vinyl alcohol copolymer, polyethylene, polypropylene, ethylene-vinyl acetate copolymer, polyamide, polyurethane, polystyrene, polyvinyl alcohol, polyvinyl chloride, polyvinylidene chloride, and polycarbonate. Among these thermoplastic resins, polyethylene terephthalate, polyacrylonitrile, ethylene-vinyl alcohol copolymer, polyethylene, polypropylene, and ethylene vinyl acetate copolymer are preferred, for example. When a resin layer formed of a thermoplastic resin is provided as the moisture barrier layer 212, one such resin layer may be formed, or two or more such resin layers may be formed using the same or different resins.

When a resin layer formed of a thermoplastic resin is provided as the moisture barrier layer 212, the thickness per layer may be determined as appropriate in accordance with the number of layers constituting the moisture barrier layer 212 and the like; for example, the thickness is 10 to 100 μm, preferably 15 to 70 μm, and more preferably 20 to 50 μm.

While the material constituting the vapor-deposited film used as the moisture barrier layer 212 is not particularly limited so long as it can block penetration of moisture, examples of materials include metals such as aluminum, chromium, zinc, gold, silver, platinum, and nickel; inorganic oxides such as silicon dioxide, titanium oxide, aluminum oxide, and zirconium oxide; and inorganic fluorides such as magnesium fluoride.

While the thickness of the vapor-deposited film is not particularly limited so long as it can suppress penetration of moisture, it is, for example, 50 to 5000 angstroms, and preferably 100 to 1000 angstroms.

The vapor-deposited film can be formed by depositing any of the above-described materials onto the resin layer formed of a thermoplastic resin or the moisture absorption layer 211, using a known vapor deposition method such as physical vapor deposition or chemical vapor deposition.

Examples of the metal foil film used as the moisture barrier layer 212 include an aluminum foil film and a stainless steel foil film. Among these metal foil films, an aluminum foil film is preferred, for example.

While the thickness of the metal foil film is not particularly limited, it is, for example, 5 to 50 µm, and preferably 5 to 15 µm.

The metal foil film can be laminated to the resin layer formed of a thermoplastic resin or the moisture absorption layer 211 in accordance with a known lamination method such as dry lamination, extrusion lamination, or thermal lamination.

The skin attachment surface-side packaging material 21 may also have a warming agent barrier function to block penetration of the warming agent contained in the moisture absorption layer 211 and/or the adhesive layer 3. This warming agent barrier function can prevent transfer of the warming agent contained in the moisture absorption layer 211 and/or the adhesive layer 3 opposite to the skin attachment surface, which allows the persistence of the warm sensation to be further improved, and allows a significant heating effect to be markedly exerted.

To provide the warming agent barrier function for the skin attachment surface-side packaging material 21, for example, at least one layer constituting the moisture barrier layer 212 may be formed of a material having both the moisture barrier function and the warming agent barrier function. Specific examples of the moisture barrier layer 212 having the warming agent barrier function include a resin layer formed of a thermoplastic resin having the warming agent barrier function (hereinafter sometimes referred to as the "warming agent barrier resin"), the vapor-deposited film, and the metal foil film.

While the warming agent barrier resin is not particularly limited in type so long as it can block penetration of the warming agent, examples of warming agent barrier resins include polyethylene terephthalate, polyacrylonitrile, and ethylene-vinyl alcohol copolymer. Among these warming agent barrier resins, polyethylene terephthalate is preferred, for example.

Furthermore, when a moisture barrier layer 212a formed of a warming agent barrier resin is provided, it is preferred that a moisture barrier layer 212b formed of a thermoplastic resin having excellent heat sealability be laminated in advance to the moisture barrier layer 212a. Specific examples of such thermoplastic resins having excellent heat sealability include polyethylene and polypropylene. Furthermore, when a laminate of the moisture barrier layer 212a formed of a warming agent barrier resin and the moisture barrier layer 212b formed of a thermoplastic resin having excellent heat sealability is used as the moisture barrier layer 212, the moisture barrier layer 212a formed of a warming agent barrier resin is preferably disposed near the skin attachment surface.

Suitable layer structures of the skin attachment surface-side packaging material 21 include a laminated structure in which the moisture barrier layer 212b formed of a thermoplastic resin having excellent heat sealability (polyethylene and/or polypropylene), the moisture barrier layer 212a formed of a warming agent barrier resin, and the moisture absorption layer 211 are laminated in this order from the housing portion 22 toward the adhesive layer 3; and a laminated structure in which the moisture barrier layer 212b formed of polyethylene and/or polypropylene, the vapor-deposited film, or the metal foil film, and the moisture absorption layer 211 are laminated in this order from the housing portion 22 toward the adhesive layer 3.

In the housing 2, a packaging material 23 disposed opposite to the skin attachment surface (hereinafter sometimes referred to as the "non-skin attachment surface-side packaging material") may be formed of the same material as that of a non-skin attachment surface-side packaging material of the packaging material 2 used in a conventional heat-generating device. When an exothermic composition that generates heat upon contact with oxygen is used as the heat-generating portion 1, the non-skin attachment surface-side packaging material 23 needs to be air-permeable; however, when a composition other than the exothermic composition is used as the heat-generating portion 1, the non-skin attachment surface-side packaging material 23 may be either air-permeable or air-impermeable.

The non-skin attachment surface-side packaging material 23 that is air-permeable may be formed of an air-permeable resin layer 231 and a fibrous base material 232, for example.

Examples of resins constituting the air-permeable resin layer 231 used to form the non-skin attachment surface-side packaging material 23 that is air-permeable include, although not particularly limited to, thermoplastic resins. Specific examples of thermoplastic resins include polyethylene, polypropylene, ethylene-vinyl acetate copolymer, polyethylene terephthalate, polyacrylonitrile, ethylene-vinyl alcohol copolymer, polyamide, polyurethane, polystyrene, polyvinyl alcohol, polyvinyl chloride, polyvinylidene chloride, and polycarbonate. Among these thermoplastic resins, polyethylene, polypropylene, and ethylene-vinyl acetate copolymer are preferred, for example.

The air-permeable resin layer 231 may specifically be a resin film provided with pores to ensure air permeability. The shape, size, and number of pores provided in the resin film may be determined as appropriate in accordance with the degree of air permeability to be imparted to the housing 2.

While the thickness of the air-permeable resin layer 231 may be determined as appropriate in accordance with the layer structure and the like of the non-skin attachment surface-side packaging material 23, it is, for example, 15 to 150 µm, preferably 30 to 100 µm, and more preferably 50 to 80 µm.

Specific examples of the fibrous base material 232 used in the non-skin attachment surface-side packaging material 23 include nonwoven fabrics and woven fabrics. The fibrous base material 232 is preferably a nonwoven fabric, for example, from the viewpoint of the feel in use and the like. Examples of materials constituting the fibrous base material 232 include, although not particularly limited to, synthetic fibers such as polyethylene terephthalate, polybutylene terephthalate, nylon, polypropylene, polyethylene, vinylon, rayon, acrylic, acetate, and polyvinyl chloride; natural fibers such as cotton, hemp, silk, and paper; and mixtures of these fibers. Among these materials, polyethylene terephthalate, nylon, and polypropylene are preferred, and polyethylene terephthalate and nylon are more preferred, for example, from the viewpoint of enhancing the feel in use.

While the weight per unit area of the fibrous base material 232 may be determined as appropriate in accordance with the layer structure and the like of the non-skin attachment surface-side packaging material, it is, for example, 1 to 100 g/m², preferably 5 to 70 g/m², and more preferably 10 to 50 g/m².

Specific layer structures of the non-skin attachment surface-side packaging material 23 that is air-permeable include a single layer structure composed of the air-permeable resin layer 231 or the fibrous base material 232; and a multilayer structure composed of layers of the same material or a combination of two or more different materials of the air-permeable resin layer 231 and the fibrous base material 232. From the viewpoint of enhancing the feel in use, and preventing leakage of the exothermic composition, for example, preferred layer structures include a single layer structure composed of the air-permeable resin layer 231; and a laminated structure in which the air-permeable resin layer 231 and the fibrous base material 232 are laminated in this order from the inside of the housing 2 toward the outside.

The air-permeable resin layer 231 and the fibrous base material 232 can be laminated to each other, using a known lamination method such as dry lamination, extrusion lamination, or thermal lamination.

Furthermore, when the non-skin attachment surface-side packaging material 23 is designed to be air-impermeable, the layer structure, the material to be used, and the like may be the same as those described for the skin attachment surface-side packaging material 21. However, the vapor-deposited film and the metal foil film are not required in the non-skin attachment surface-side packaging material 23 that is air-impermeable.

The housing 2 used in the present invention is formed by bonding the skin attachment surface-side packaging material 21 and the non-skin attachment surface-side packaging material 23 around the region that defines the housing portion 22 that contains the heat-generating portion 1.

Examples of methods for bonding the skin attachment surface-side packaging material 21 and the non-skin attachment surface-side packaging material 23 include, although not particularly limited to, a method that involves heat-sealing them by using the moisture barrier layer 212 included in the skin attachment surface-side packaging material 21 and/or the resin layer included in the non-skin attachment surface-side packaging material 23; and a method that involves bonding them with an adhesive.

When an exothermic composition that generates heat upon contact with oxygen is used as the heat-generating portion 1, the amount of the exothermic composition to be contained in the housing portion 22 of the housing 2 may be determined as appropriate in accordance with the skin site to which the heat-generating device is to be attached, the heat-generating properties of the exothermic composition, and the like; for example, the amount of the exothermic composition may be about 0.01 to 1.5 g, preferably about 0.05 to 1 g, and more preferably about 0.1 to 0.8 g, per cm² area of the skin attachment surface-side packaging material 21 in the region that forms the housing portion 22.

In the housing 2 used in the present invention, the number of housing portions 22 that contain the heat-generating portion 1 is not particularly limited, and may be one or more than one, and is determined as appropriate in accordance with the skin site to which the heat-generating device is to be attached, for example. Furthermore, the size or the shape of the housing portion 22 is not particularly limited, and may be determined as appropriate in accordance with the shape of the skin site to which the heat-generating device is to be attached, for example.

<Adhesive Layer 3>

In the heat-generating device of the present invention, the adhesive layer 3 is partially provided on the surface of the moisture absorption layer 211 (i.e., on the skin attachment surface of the housing 2). When the adhesive layer 3 is thus partially provided, the region where the adhesive layer 3 is formed (hereinafter sometimes referred to as the "adhesive layer formation region 3X") and the region where the moisture absorption layer 211 is exposed (hereinafter, the "moisture absorption layer exposure region 211X") are formed on the skin attachment surface of the heat-generating device of the present invention. The adhesive layer formation region 3X serves to fix the heat-generating device to the skin, and the moisture absorption layer exposure region 211X serves to absorb sweat.

The adhesive layer 3 is formed using an adhesive as a base. An adhesive refers to a composition containing a polymer that exhibits adhesion (adhesive polymer) in the presence of an oil or another solvent, for example, wherein the adhesive polymer is dispersed or dissolved in the oil or other solvent, for example, such that the composition exhibits adhesion. Types or compositions of such adhesive polymers contained in adhesives are known, and adhesives used in adhesive layers for conventional disposable body warmers can be used in the present invention. Specific examples of types of adhesives include rubber-based adhesives, acrylic-based adhesives, silicone-based adhesives, and urethane-based adhesives.

Specific examples of adhesive polymers contained in rubber-based adhesives include polystyrene-polybutadiene-polystyrene-based copolymer, polystyrene-polyisoprene-polystyrene-based copolymer, polystyrene-polyethylene-polybutylene-polystyrene copolymer, and polystyrene-polyethylene-polypropylene-polystyrene copolymer.

Specific examples of silicone-based adhesives include addition reaction-curing silicone-based adhesives and peroxide-curing silicone-based adhesives.

Specific examples of adhesive polymers contained in acrylic-based adhesives include (meta)acrylic polymers containing acrylic monomers as structural units, such as methyl acrylate, ethyl acrylate, 2-ethylhexyl acrylate, and butyl acrylate.

Specific examples of adhesive polymers contained in urethane-based adhesives include urethane resins obtained by reacting polyols such as polyether polyols, polyester polyols, polycarbonate polyols, and polycaprolactone polyols with polyisocyanates such as diphenylmethane diisocyanate, tolylene diisocyanate, and hexamethylene diisocyanate.

These adhesives may be used alone, or in combination of two or more.

Among these adhesives, rubber-based adhesives are preferred, for example.

The adhesive layer 3 may be formed of an adhesive only, or may contain other components such as the warming agent described below.

When the adhesive layer 3 contains components other than an adhesive, the content of the adhesive in the adhesive layer 3 may be determined as appropriate in accordance with the adhesion to the skin, the ratio of the adhesive layer formation region, and the like; for example, the content is 60 to 99.9 wt %, preferably 70 to 99 wt %, and more preferably 80 to 98 wt %.

The adhesive layer 3 is preferably provided at least within a bottom surface region of the housing portion 22 that contains the heat-generating portion 1 in the housing 2. While the shape of the adhesive layer formation region of the adhesive layer 3 is not particularly limited so long as the adhesive layer 3 is partially provided on the surface of the moisture absorption layer 211, examples of shapes include a stripe shape, a dot shape, a grid shape, a mesh shape, and a frame shape surrounding the edge of the moisture absorption layer.

FIG. 1 shows an exemplary embodiment in which the adhesive layer formation region 3X is formed in the form of stripes. When the adhesive layer formation region is formed in the form of stripes, the stripe width of the adhesive layer formation region 3X may be determined as appropriate in accordance with the skin site to which the heat-generating device is to be attached, the size of the heat-generating device, and the like; for example, the stripe width is about 1 to 100 mm, and preferably about 3 to 30 mm.

Figure 2:
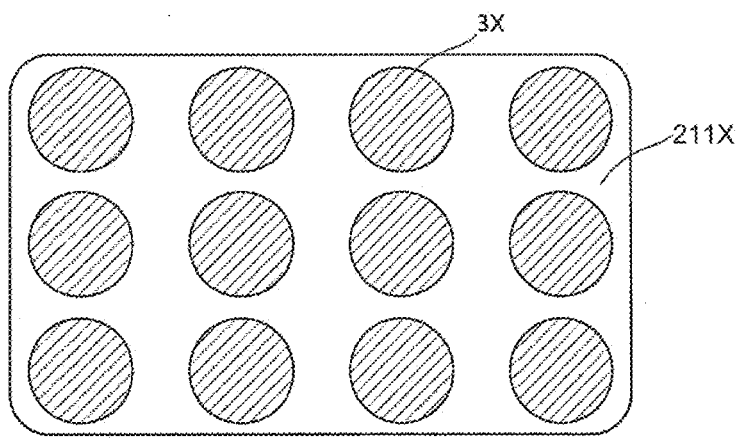
FIG. 2 is a schematic plan view of a heat-generating device in which an adhesive layer is provided in the form of dots on a surface of a moisture absorption layer, as seen from the skin attachment surface.

FIG. 2 shows an exemplary embodiment in which the adhesive layer formation region 3X is formed in the form of dots. While FIG. 2 shows an embodiment in which circular dots are arranged, the dot shape may be any of oval, polygonal, indefinite, and the like. When the adhesive layer formation region 3X is formed in the form of dots, the area per dot may be determined as appropriate in accordance with the skin site to which the heat-generating device is to be attached, the size of the heat-generating device, and the like; for example, the area per dot is about 5 to 10000 mm$^2$, and preferably about 500 to 3000 mm$^2$.

Figure 3:
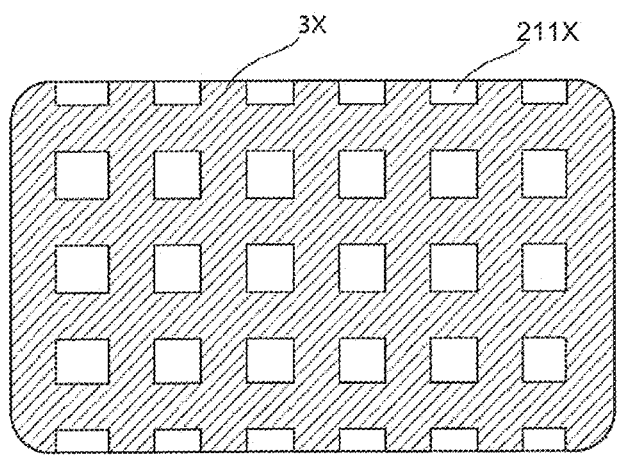
FIG. 3 is a schematic plan view of a heat-generating device in which an adhesive layer is provided in the form of a grid on a surface of a moisture absorption layer, as seen from the skin attachment surface.

FIG. 3 shows an exemplary embodiment in which the adhesive layer formation region 3X is formed in the form of a grid. When the adhesive layer formation region 3X is formed in the form of a grid, the area per square may be determined as appropriate in accordance with the skin site to which the heat-generating device is to be attached, the size of the heat-generating device, and the like; for example, the area per square is about 1 to 3000 mm$^2$, and preferably about 10 to 1000 mm$^2$.

Figure 4:
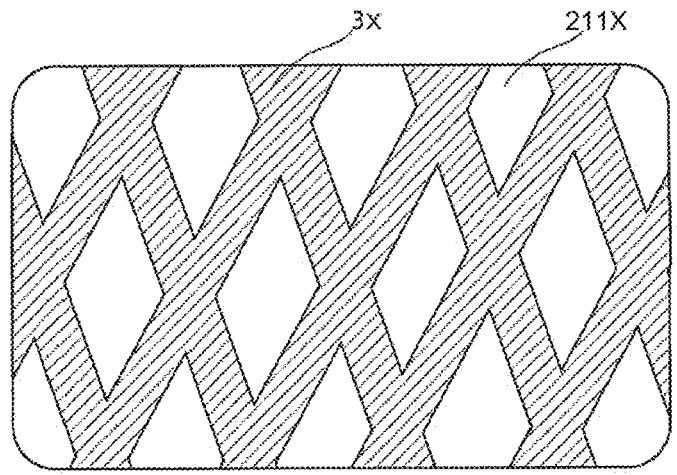
FIG. 4 is a schematic plan view of a heat-generating device in which an adhesive layer is provided in the form of a mesh on a surface of a moisture absorption layer, as seen from the skin attachment surface.

FIG. 4 shows an exemplary embodiment in which the adhesive layer formation region 3X is formed in the form of a mesh. When the adhesive layer formation region 3X is formed in the form of a mesh, the line width forming the mesh may be determined as appropriate in accordance with the skin site to which the heat-generating device is to be attached, the size of the heat-generating device, and the like; for example, the line width is about 1 to 100 mm, and preferably about 3 to 30 mm.

Figure 5:
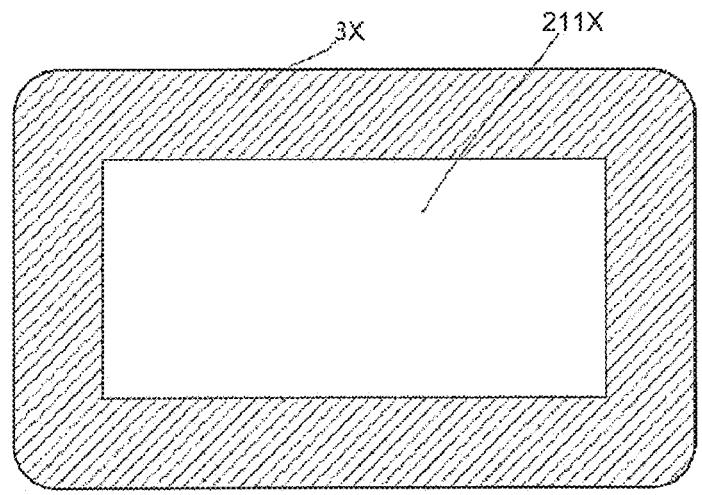
FIG. 5 is a schematic plan view of a heat-generating device in which an adhesive layer is provided in the form of a frame on a surface of a moisture absorption layer, as seen from the skin attachment surface.

FIG. 5 shows an exemplary embodiment in which the adhesive layer formation region 3X is formed in the form of a frame. When the adhesive layer formation region 3X is formed in the form of a frame, the width of the frame may be determined as appropriate in accordance with the skin site to which the heat-generating device is to be attached, the size of the heat-generating device, and the like; for example, the width of the frame is about 1 to 100 mm, and preferably about 3 to 50 mm.

The moisture absorption layer exposure region 211X formed preferably communicates with the edge of the moisture absorption layer 211. When the moisture absorption layer exposure region 211X communicates with the edge of the moisture absorption layer 211, a path through which air flows can be ensured when the heat-generating device is attached to the skin, which allows stickiness due to sweat during use to be suppressed even more effectively. Specific examples of embodiments in which the moisture absorption layer exposure region 211X communicates with the edge of the moisture absorption layer 211 include an embodiment in which the adhesive layer 3 is formed in the form of stripes or dots.

The area ratio of the adhesive layer formation region 3X to the moisture absorption layer exposure region 211X may be determined as appropriate in accordance with the adhesion to the skin to which the heat-generating device is to be attached and the like; for example, the area ratio of the adhesive layer formation region 3X to the moisture absorption layer exposure region 211X is typically 100:5-2000, preferably 100:10-400, more preferably 100:25-150, and particularly preferably 100:25-66.7.

The amount of the adhesive layer 3 to be applied may be determined as appropriate in accordance with the adhesion to the skin to which the heat-generating device is to be attached, the ratio of the adhesive layer formation region 3X, and the like; for example, the amount of the adhesive layer 3 to be applied in the adhesive layer formation region 3X is typically 20 to 150 g/m$^2$, preferably 40 to 120 g/m$^2$, and more preferably 60 to 100 g/m$^2$.

The adhesive layer 3 is formed by application to the moisture absorption layer 211 of the skin attachment surface-side packaging material 21 constituting the housing 2, using a known coating method.

<Warming Agent>

In the heat-generating device of the present invention, a warming agent that allows an enhanced warm sensation to be perceived in the presence of moisture is contained in at least one of the adhesive layer 3 and the moisture absorption layer 211. The warming agent imparts a warm sensation, and contributes to the exertion of an excellent heating effect.

The "warming agent that allows an enhanced warm sensation to be perceived in the presence of moisture" refers to a warming agent that allows a perceived warm sensation to be enhanced in the presence of moisture, compared to that in the absence of moisture, among warming agents that impart a warm sensation to the skin. While the warming agent that allows an enhanced warm sensation to be perceived in the presence of moisture is known in the art, and is not particularly limited in type, specific examples of warming agents include capsaicin, nonanoic acid vanillylamide, sage, caffeine, tocopherol nicotinate, nicotinic acid benzyl ester, vanillyl ethyl ether, vanillyl propyl ether, vanillyl butyl ether, vanillyl pentyl ether, vanillyl hexyl ether, vanillyl butyl ether acetate, gingerol, *Capsicum annuum* extract, and ginger extract.

These warming agents may be used alone, or in combination of two or more.

Among the warming agents, *Capsicum annuum* extract is a component obtained by extraction treatment of *Capsicum annuum*. *Capsicum annuum* to be used as the raw material of the *Capsicum annuum* extract may be in a dried or undried state. *Capsicum annuum* to be used as the raw material of the *Capsicum annuum* extract may also be subjected to a treatment such as pulverization or chopping. Furthermore, *Capsicum annuum* to be used as the raw material of the *Capsicum annuum* extract may also be subjected to an enzyme treatment in advance, using an enzyme such as a carbohydrase, a protease, a lipase, or a nuclease.

Specific examples of extraction solvents used for the extraction treatment of *Capsicum annuum* include water and hydrated ethanol (ethanol content: about 30 to 95 wt %).

While the conditions for the extraction treatment of *Capsicum annuum* are not particularly limited, the extraction treatment may be performed, for example, for about 10 seconds to 24 hours, preferably about 1 minute to 6 hours, using about 100 to 100000 ml, preferably about 100 to 10000 ml, of an extraction solvent per kg of *Capsicum annuum*, at a temperature of about 5 to 120° C., preferably about 10 to 70° C.

The extract obtained by the extraction treatment of *Capsicum annuum* is concentrated or dried to obtain *Capsicum annuum* extract. The extract obtained by the extraction treatment of *Capsicum annuum* may be subjected to a treatment such as removal of insoluble substances or sterilization, as required.

While the *Capsicum annuum* extract to be used as the warming agent may be in a dried state or a hydrous state, it is preferably in a dried state.

Among the warming agents, ginger extract is a component obtained by extraction treatment of ginger. The ginger to be used as the raw material of the ginger extract may be in a dried or undried state. The ginger to be used as the raw material of the ginger extract may also be subjected to a treatment such as pulverization or chopping. Furthermore, the ginger to be used as the raw material of the ginger extract may also be subjected to an enzyme treatment in advance, using an enzyme such as a carbohydrase, a protease, a lipase, or a nuclease.

Specific examples of extraction solvents used for the extraction treatment of ginger include water and hydrated ethanol (ethanol content: about 30 to 95 wt %).

While the conditions for the extraction treatment of ginger are not particularly limited, the extraction treatment may be performed, for example, for about 10 seconds to 24 hours, preferably about 1 minute to 6 hours, using about 100 to 100000 ml, preferably about 100 to 10000 ml, of an extraction solvent per kg of ginger, at a temperature of about 5 to 120° C., preferably about 10 to 70° C.

The extract obtained by the extraction treatment of ginger is concentrated or dried to obtain ginger extract. The extract obtained by the extraction treatment of ginger may be subjected to a treatment such as removal of insoluble substances or sterilization, as required.

While the ginger extract to be used as the warming agent may be in a dried state or a hydrous state, it is preferably in a dried state.

Among these warming agents, capsaicin, nonanoic acid vanillylamide, and ginger extract are preferred, for example, from the viewpoint of further improving the persistence of the warm sensation to be perceived, and exerting a higher heating effect.

The warming agent may be contained in either one of the adhesive layer 3 and the moisture absorption layer 211, or may be contained in both these layers. The warming agent is preferably contained at least in the adhesive layer 3, from the viewpoint of further enhancing the warm sensation to be perceived, and further improving the heating effect.

The content of the warming agent in the adhesive layer 3 and/or the moisture absorption layer 211 may be determined as appropriate in accordance with the type of the warming agent to be used, the type of the layer that is to contain the warming agent, and the like. When the warming agent is to be contained in the adhesive layer 3, the content of the warming agent in the adhesive layer 3 is, for example, 0.0001 to 10 wt %, preferably 0.0005 to 8 wt %, and more preferably 0.001 to 5 wt %. The content of the warming agent represents a value calculated on a dry weight basis, where an extract is used. When the warming agent is to be contained in the moisture absorption layer 211, the amount of the warming agent to be contained per unit area of the moisture absorption layer 211 is, for example, 0.0005 to 500 mg/cm$^2$, preferably 0.001 to 300 mg/cm$^2$, and more preferably 0.005 to 150 mg/cm$^2$.

When the warming agent is to be contained in the adhesive layer 3, an adhesive layer composition may be prepared by mixing the warming agent and an adhesive used as a base of the adhesive layer 3, and applying the composition onto the moisture absorption layer 211. When the warming agent is to be contained in the moisture absorption layer 211, the warming agent may be loaded into the moisture absorption layer, using, for example, a method that involves spraying a solution containing the warming agent onto the moisture absorption layer 211 or a method that involves immersing the moisture absorption layer 211 in a solution containing the warming agent.

<Other Components>

The adhesive layer 3 and/or the moisture absorption layer 211 may contain other pharmacological components and cosmetic components, as required, in addition to the warming agent. Examples of such pharmacological components and cosmetic components include blood circulation promoters such as acid mucopolysaccharides, chamomile, *Aesculus hippocastanum*, ginkgo, *Hamamelis virginiana* extract, grapefruit extract, rosemary extract, lemon extract, vitamin E, and nicotinic acid derivatives; moisturizers such as glycerol, ceramide, collagen, hyaluronic acid, and squalane; fatigue recovery agents such as basil extract and juniper extract; analgesics such as indomethacin, diclofenac, flurbiprofen, ketoprofen, piroxicam, felbinac, methyl salicylate, and glycol salicylate; slimming agents such as tea extract, ginseng root extract, *Aesculus hippocastanum*, aminophylline, aescin, anthocyanidin, organic iodine compounds, *Hypericum perforatum* extract, *Filipendula multijuga* extract, *Equisetum arvense, Rosmarinus officinalis, Hedera helix*, thiomucase, and hyaluronidase; edema-reducing agents such as *Terminalia sericea, Ammi visnaga, Ammi majus, Aesculus hippocastanum*, anthocyanin, vitamin P, *Calendula officinalis*, concholytic acid, and silanol; peeling agents such as proteases; hair-removing agents such as calcium thioglycolate; autonomic nerve-regulating agents such as γ-oryzanol; and fragrances such as natural fragrances and single fragrances.

While these pharmacological components and cosmetic components may be contained in any of the adhesive layer 3 and the moisture absorption layer 211, they are preferably contained in the adhesive layer 3, from the viewpoint of effectively achieving their pharmacological effects or cosmetic effects.

These pharmacological components and cosmetic components may be used alone, or in combination of two or more. The content of the pharmacological components and cosmetic components in the adhesive layer 3 and/or the moisture absorption layer 211 may be determined as appropriate in accordance with the pharmacological effects or cosmetic effects to be imparted. The method for incorporating these components into the adhesive layer 3 and/or the moisture absorption layer 211 is the same as that described for the warming agent.

<Release Layer>

In the heat-generating device of the present invention, a releasable release layer may be provided, as required, on the surface (the side to be attached to the skin) of the adhesive layer 3. When the release layer is provided, it can prevent the adhesive layer during storage from drying, prevent volatilization of the warming agent during storage, and prevent a decrease in handleability due to the adhesion of the adhesive layer, for example.

Examples of release layers include resin films such as polyethylene terephthalate, polyacrylonitrile, ethylene-vinyl alcohol copolymer, and polypropylene; and paper that has been subjected to a treatment for imparting release properties, such as a silicone treatment. When a resin film is used as the release layer, the resin film may be subjected to a treatment for imparting release properties, such as a silicone treatment. Among these release layers, resin films such as polyethylene terephthalate, polyacrylonitrile, and ethylene-vinyl alcohol copolymer are suitable in that they can suppress adsorption of the active ingredient in the adhesive layer 3.

<Preferred Embodiments>

Figure 6:
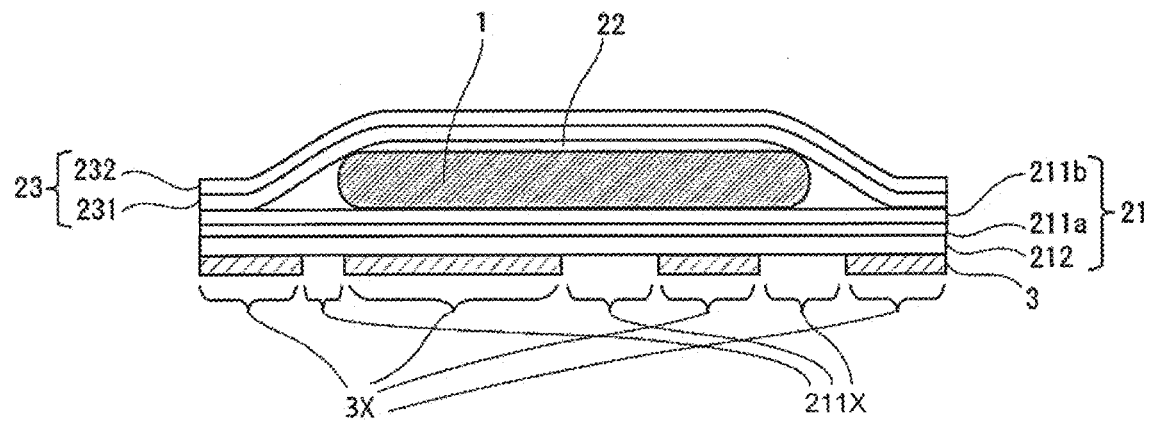
FIG. 6 is a schematic view of a cross-sectional structure of one preferred embodiment of the heat-generating device of the present invention.

FIG. 6 shows a schematic view of a cross-sectional structure of one preferred embodiment of the heat-generating device of the present invention. In the heat-generating device shown in FIG. 6, the edge of the skin attachment surface-side packaging material 21 and the edge of the non-skin attachment surface-side packaging material 23 are bonded with each other to form the housing 2 having the housing portion 22. As a result, an exothermic composition that generates heat upon contact with oxygen is contained as the heat-generating portion 1 in the housing 2. In the heat-generating device shown in FIG. 6, the skin attachment surface-side packaging material 21 of the housing 2 is composed of a laminated sheet in which the moisture barrier layer 212b formed of a thermoplastic resin having excellent sealability (polyethylene and/or polypropylene), the moisture barrier layer 212a formed of a warming agent barrier resin, and the moisture absorption layer 211 are laminated in this order from the housing portion 22 toward the skin attachment surface. Moreover, in the heat-generating device shown in FIG. 6, the non-skin attachment surface-side packaging material 23 of the housing 2 is formed of a laminated sheet in which the air-permeable resin layer 231 and the fibrous base material 232 are laminated in this order from the housing portion 22 toward the outside. Furthermore, in the heat-generating device shown in FIG. 6, the adhesive layer 3 is partially provided on the surface of the moisture absorption layer 211 constituting the skin attachment surface-side packaging material 21. In FIG. 6, the release layer is not shown for convenience sake.

<Modes of Use and Packaging Forms>

The heat-generating device of the present invention is used as a warming device or a therapeutic device for the body, by attaching the adhesive layer to the skin. In particular, since the heat-generating device of the present invention can exert a markedly high heating effect, it is particularly suitable for use as a therapeutic device for promoting blood circulation, relieving pain, reducing stiff shoulders, and the like.

Examples of skin sites to which the heat-generating device of the present invention is to be applied include, although not particularly limited to, eye, face, neck, shoulder, waist, back, abdomen, buttocks, arm, leg, and sole.

When the heat-generating portion 1 is an exothermic composition that generates heat upon contact with oxygen, the heat-generating device of the present invention is packaged in a packaging material having oxygen barrier properties, and provided in a state where the exothermic composition is not brought into contact with air. When the packaging material is opened at the time of use, the exothermic composition is brought into contact with air, and initiates heat generation.

EXAMPLES

The present invention will be hereinafter described in more detail with reference to examples, which are not intended to limit the present invention.

Test Example 1

Heat-generating devices (Examples 1 to 4 and Comparative Examples 1 to 6) having different area ratios of the adhesive layer formation region to the moisture absorption layer exposure region were produced, and each of the heat-generating devices was evaluated for the persistence of the warm sensation, adhesion to the skin, and feel in use. The method for producing each of the heat-generating devices, evaluation methods, and the like are as described below.

1. Production of Heat-Generating Devices

Example 1

A skin attachment surface-side packaging material (a rectangle with a length of 13 cm and a width of 9.5 cm) was prepared which was formed of an air-impermeable laminated sheet in which a polyethylene film, a polyethylene terephthalate film, and a nonwoven fabric (made of polyethylene terephthalate) were laminated in this order. An adhesive layer-forming composition A of the composition shown below, which was prepared by mixing the components while heating at 140° C., was applied partially to the surface of the nonwoven fabric of the skin attachment surface-side packaging material such that the amount of the adhesive layer formation region applied was 100 g/m$^2$, and then the composition was cooled to partially form an adhesive layer on the skin attachment surface-side packaging material. The partial formation of the adhesive layer was performed such that the adhesive layer formation region was formed in the form of four stripes in the longitudinal direction, and the moisture absorption layer (nonwoven fabric) exposure region was formed in the form of three stripes, each between the stripes of the adhesive layer formation region, wherein the stripe width of the adhesive layer formation region was 19 mm, the width of the moisture absorption layer (nonwoven fabric) exposure region was 6.3 mm, and the area ratio of the adhesive layer formation region to the moisture absorption layer exposure region was 80:20.

| <Adhesive Layer-Forming Composition A> | |
|---|---|
| Capsaicin (trade name "Capsaicin" from Alps Pharmaceutical Ind. Co., Ltd.) | 0.01 wt % |
| Rubber-based adhesive | 99.99 wt % |
| Total | 100 wt % |

Next, a release layer formed of a silicone-treated polyethylene terephthalate film (a rectangle with a length of 13 cm and a width of 9.5 cm) was bonded to the adhesive layer on the skin attachment surface-side packaging material.

Separately, a non-skin attachment surface-side packaging material (a rectangle with a length of 13 cm and a width of 9.5 cm) was prepared which was formed of an air-permeable laminated sheet in which a polyethylene film with pores and a nonwoven fabric (made of polyethylene terephthalate) were laminated.

Next, an exothermic composition was prepared by mixing 22 g of an iron powder, 6 g of activated carbon, and 10 g of a water-soluble salt/water-retaining agent/water mixture (a mixture of sodium chloride, a water-absorbing resin, vermiculite, water, and the like; water content: 8.5 g). With 38 g of the resulting exothermic composition being sandwiched between the polyethylene film of the skin attachment surface-side packaging material and the polyethylene film of the non-skin attachment surface-side packaging material, the edges of these packaging materials were heat-sealed to produce a heat-generating device containing the exothermic composition in a housing portion (length: 12 cm, width: 8.5 cm). The heat-generating device thus produced was rapidly placed in a hermetic bag.

Example 2

A heat-generating device was produced under the same conditions as those in Example 1 above, except that the partial formation of the adhesive layer on the skin attachment surface-side packaging material was performed such that the stripe width of the adhesive layer formation region was 14.25 mm, the width of the moisture absorption layer (nonwoven fabric) exposure region was 12.7 mm, and the area ratio of the adhesive layer formation region to the moisture absorption layer exposure region was 60:40.

Example 3

A heat-generating device was produced under the same conditions as those in Example 1 above, except that the partial formation of the adhesive layer on the skin attachment surface-side packaging material was performed such that the stripe width of the adhesive layer formation region was 9.5 mm, the width of the moisture absorption layer (nonwoven fabric) exposure region was 19 mm, and the area ratio of the adhesive layer formation region to the moisture absorption layer exposure region was 40:60.

Comparative Example 1

A heat-generating device was produced under the same conditions as those in Example 1 above, except that the adhesive layer formation region was formed over the entire surface of the nonwoven fabric of the skin attachment surface-side packaging material (i.e., the area ratio of the adhesive layer formation region to the moisture absorption layer exposure region was 100:0).

2. Performance Evaluation

Each of the heat-generating devices was attached to waist parts of ten subjects. After two hours from the attachment, the perceived warm sensation, the adhesion to the skin, and the feel in use were scored in accordance with the following determination criteria. For each item of evaluation, an average score of 2 points or more and 3 points or less was determined as "A", an average score of 1 point or more and less than 2 points was determined as "B", an average score of 0.5 point or more and less than 1 point was determined as "C", and an average score of less than 0.5 point was determined as D.

(Determination Criteria for Warm Sensation)
3 Points: The warm sensation is sufficiently perceived.
2 Points: The warm sensation is perceived.
1 Point: The warm sensation is weakly perceived.
0 Point: The warm sensation is not perceived.
(Determination Criteria for Adhesion to Skin)
3 Points: No removal or the like at the edge is observed, and sufficient adhesion is maintained.
2 Points: Slight removal or the like at the edge is observed, but sufficient adhesion is maintained.
1 Point: Removal or the like at the edge is observed, and the adhesion is slightly unstable.
0 Point: Significant removal or the like at the edge is observed, and the adhesion is unstable.

(Determination Criteria for Feel in Use)
3 Points: No stickiness due to sweat is felt, and the feel in use is excellent.
2 Points: Stickiness due to sweat is slightly felt, but the feel in use is good.
1 Point: Stickiness due to sweat is felt, and the feel in use is slightly poor.
0 Point: Stickiness due to sweat is strongly felt, and the feel in use is poor.

3. Evaluation Results

The results are shown in Table 1. As is clear from Table 1, in the case of the heat-generating device in which the adhesive layer was formed over the entire surface of the skin attachment surface of the skin attachment surface-side packaging material, the persistence of the warm sensation (the warm sensation after two hours from the attachment) was poor, and the adhesion to the skin and the feel in use were unsatisfactory (Comparative Example 1). In contrast, in the case of the heat-generating devices in which the adhesive layer was partially provided on the skin attachment surface of the skin attachment surface-side packaging material, the persistence of the warm sensation was improved, and the adhesion to the skin and the feel in use were also improved (Examples 1 to 3). In particular, in the case of the heat-generating devices in which the area ratio of the adhesive layer formation region to the moisture absorption layer exposure region was 80:20 to 60:40, the persistence of the warm sensation was markedly high, and the adhesion to the skin and the feel in use were good.

TABLE 1

| | Area Ratio of Adhesive Layer Formation Region to Moisture Absorption Layer Exposure Region | Warm Sensation | Adhesion to Skin | Feel in Use |
| --- | --- | --- | --- | --- |
| Example 1 | 80:20 | A | A | B |
| Example 2 | 60:40 | A | A | A |
| Example 3 | 40:60 | A | B | A |
| Comparative Example 1 | 100:0 | C | B | D |

Test Example 2

Heat-generating devices (Examples 2 and 4 and Comparative Examples 2 to 6) having different structures of the skin attachment surface-side packaging material and having different components contained in the adhesive layer were produced, and each of the heat-generating devices was evaluated for the persistence of the warm sensation, adhesion to the skin, and feel in use. The method for producing each of the heat-generating devices of Example 4 and Comparative Examples 2 to 6, evaluation methods, and the like are as described below.

1. Production of Heat-Generating Devices

Example 4

A heat-generating device was produced under the same conditions as those described in Example 2 above, except that an adhesive layer was formed using an adhesive layer-forming composition B of the composition shown below.

| <Adhesive Layer-Forming Composition B> | |
|---|---|
| Nonanoic acid vanillylamide (trade name "Nonanoic acid vanillylamide" from Nagaoka & Co., Ltd.) | 0.001 wt % |
| Rubber-based adhesive | 99.999 wt % |
| Total | 100 wt % |

Comparative Example 2

A skin attachment surface-side packaging material (a rectangle with a length of 13 cm and a width of 9.5 cm) was prepared which was formed of an air-impermeable laminated sheet in which a polyethylene film and a polyethylene terephthalate film were laminated in this order. A heat-generating device was produced under the same conditions as those described in Example 2 above, except that an adhesive layer was partially formed on the surface of the polyethylene terephthalate film of the skin attachment surface-side packaging material.

Comparative Example 3

An air-permeable skin attachment surface-side packaging material (a rectangle with a length of 13 cm and a width of 9.5 cm) formed of a nonwoven fabric (made of polyethylene terephthalate) only was prepared. An adhesive layer was partially formed on one surface of the skin attachment surface-side packaging material, under the same conditions as those described in Example 2 above. Separately, a non-skin attachment surface-side packaging material (a rectangle with a length of 13 cm and a width of 9.5 cm) was prepared which was formed of an air-impermeable laminated sheet in which a polyethylene film and a nonwoven fabric (made of polyethylene terephthalate) were laminated.

Next, a heat-generating device containing the exothermic composition in a housing portion (length: 12 cm, width: 8.5 cm) was produced under the same conditions as those described in Example 2 above, except that the edge of the polyethylene film of the skin attachment surface-side packaging material and the edge of the non-skin attachment surface-side packaging material were bonded with a spray adhesive.

Comparative Example 4

A heat-generating device was produced under the same conditions as those described in Example 2 above, except that an adhesive layer was formed using an adhesive layer-forming composition C of the composition shown below.

| <Adhesive Layer-Forming Composition C> | |
|---|---|
| dl-α-Tocopherol; vitamin E (trade name "Vitamin E Linoleate Mixture" from Eisai Food & Chemical Co., Ltd.) (oily) | 5 wt % |
| Rubber-based adhesive | 95 wt % |
| Total | 100 wt % |

Comparative Example 5

A heat-generating device was produced under the same conditions as those described in Comparative Example 2 above, except that an adhesive layer was formed using the adhesive layer-forming composition C shown above.

Comparative Example 6

A heat-generating device was produced under the same conditions as those described in Example 2 above, except that an adhesive layer was formed using only the rubber-based adhesive shown above.

2. Performance Evaluation

Each of the heat-generating devices was evaluated for the persistence of the warm sensation, adhesion to the skin, feel in use, and lumbago-relieving effect. The persistence of the warm sensation was evaluated using, as a reference, the warm sensation perceived with the heat-generating device of Comparative Example 6. The adhesion to the skin and the feel in use were evaluated using the same methods as those described in Test Example 1 above. The method for evaluating the lumbago-relieving effect is as described below.

Each of the heat-generating devices was attached to waist parts of ten subjects suffering from lumbago for eight hours. After eight hours from the attachment, the lumbago-relieving effect was scored in accordance with the following determination criteria. Using an average score for Comparative Example 6 as 100, an average score of 95 points or more and less than 105 points was determined as "C", an average score of 105 points or more and less than 250 points was determined as "B", and an average score of 250 points or more and 400 points or less was determined as "A".

(Determination Criteria for Lumbago-Relieving Effect)
3 Points: Lumbago is significantly relieved.
2 Points: Lumbago is relieved.
1 Point: Lumbago is slightly relieved.
0 Point: Lumbago is not relieved.

3. Evaluation Results

The results are shown in Table 2. In the case of the heat-generating device in which a moisture absorption layer (nonwoven fabric) was not provided on the skin attachment surface-side packaging material, even though capsaicin was contained in the partially provided adhesive layer, the persistence of the warm sensation was comparable to that of Comparative Example 6 not containing capsaicin, and the adhesion to the skin, feel in use, and lumbago-relieving effect were insufficient (Comparative Example 2). Moreover, in the case of the heat-generating device in which a moisture barrier layer was not provided, even though capsaicin was contained in the partially provided adhesive layer, the persistence of the warm sensation was lower than that of Comparative Example 6, and the lumbago-relieving effect was unsatisfactory (Comparative Example 3). On the other hand, in the case of the heat-generating devices in which vitamin E known to have a blood circulation-promoting effect was contained in the partially provided adhesive layer, the persistence of the warm sensation was comparable to that of Comparative Example 6, regardless of the presence or absence of the moisture absorption layer (nonwoven fabric), and the lumbago-relieving effect was insufficient (Comparative Examples 4 and 5). In contrast, in the case of the heat-generating devices in which an adhesive layer containing a warming agent (capsaicin or nonanoic acid vanillylamide) was partially provided on the skin attachment surface-side packaging material in which the moisture absorption layer (nonwoven fabric) and the moisture barrier layer (resin film) were laminated, the persistence of the warm sensation was excellent, a markedly high lumbago-relieving effect was observed, and the adhesion to the skin and the feel in use were good (Examples 2 and 4).

TABLE 2

| | Area Ratio of Adhesive Layer Formation Region to Moisture Absorption Layer Exposure Region | Structure of Skin Attachment Surface-Side Packaging Material | | Component Contained in Adhesive Layer | Warm Sensation (Comparative Example 6 as Reference) | Adhesion to Skin | Feel in Use | Lumbago-Relieving Effect |
|---|---|---|---|---|---|---|---|---|
| | | Presence/Absence of Moisture Absorption Layer (Nonwoven Fabric) | Presence/Absence of Moisture Barrier Layer (Resin Film) | | | | | |
| Example 2 | 60:40 | Present | Present | Capsaicin | Higher than Comparative Example 6 | A | A | A |
| Example 4 | 60:40 | Present | Present | Nonanoic Acid Vanillylamide | Higher than Comparative Example 6 | A | A | A |
| Comparative Example 2 | 60:40 | Absent | Present | Capsaicin | Comparable to Comparative Example 6 | D | D | C |
| Comparative Example 3 | 60:40 | Present | Absent | Capsaicin | Lower than Comparative Example 6 | A | A | C |
| Comparative Example 4 | 60:40 | Present | Present | Vitamin E | Comparable to Comparative Example 6 | A | A | C |
| Comparative Example 5 | 60:40 | Absent | Present | Vitamin E | Comparable to Comparative Example 6 | D | D | C |
| Comparative Example 6 | 60:40 | Present | Present | None | — | A | A | — |

Test Example 3

Using six subjects, changes in blood flow rate induced by the heat-generating devices of Example 1 and Comparative Example 6 were evaluated. Specifically, the skin blood flow rate (ml/min) in a waist part of each subject was measured with time for 10 minutes. Then, each of the heat-generating devices was attached to the waist part, and changes in skin blood flow rate (ml/min) were measured with time for 50 minutes. The skin blood flow rate was measured using a laser Doppler blood flow meter (ALF21 from ADVANCE Co., Ltd.).

Figure 7:
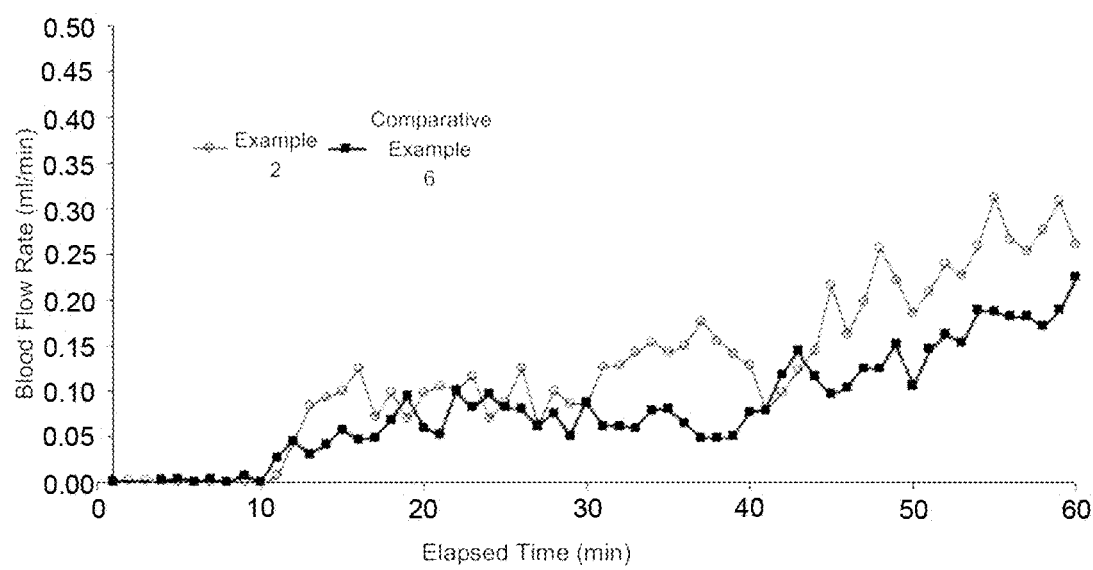
FIG. 7 is a graph showing the results obtained in Test Example 3 by attaching the heat-generating devices of Example 1 and Comparative Example 6, and measuring blood flow rate with time.

FIG. 7 shows changes with time in the average value of skin blood flow rate of the six subjects. The results confirmed that the heat-generating device of Example 1 provides an improved blood flow rate, compared to the heat-generating device of Comparative Example 1, and can exert an excellent heating effect.

REFERENCE SIGNS LIST 1 heat-generating portion
2 housing
21 skin attachment surface-side packaging material
211 moisture absorption layer
212 moisture barrier layer
212a moisture barrier layer having warming agent barrier function (resin layer)
212b moisture barrier layer having excellent heat sealability (resin layer)
22 housing portion
23 non-skin attachment surface-side packaging material
231 air-permeable resin layer
232 fibrous base material
3 adhesive layer

The invention claimed is:

1. A heat-generating device that is used by being attached to skin, comprising:
a heat-generating portion that generates heat to be delivered to skin;
a housing that contains the heat-generating portion, and has a skin attachment surface that is to be attached to the skin; and
two or more adhesive layers provided on the skin attachment surface of the housing,
wherein a packaging material constituting the skin attachment surface of the housing is formed of a laminated sheet in which at least a moisture absorption layer that absorbs moisture and a moisture barrier layer that blocks penetration of moisture are coextensive with each other and are laminated in this order from the two or more adhesive layers,
wherein the moisture barrier layer is laminated over an entire surface of a first side of the moisture absorption layer opposite from the two or more adhesive layers,
wherein the two or more adhesive layers are partially provided on portions of a surface of a second side of the moisture absorption layer, wherein the second side of the moisture absorption layer is parallel to and opposite from the moisture barrier layer, wherein a moisture absorption layer exposure region on the surface of the second side of the moisture absorption layer that is not in contact with the adhesive layers, is exposed and, together with sides of the two or more adhesive layers, perpendicular to the second side of the moisture absorption layer, and a skin surface to which the skin attachment surface is bound form one or more path(s) through which air can flow from outside the skin attachment surface to internal regions of the second side of the moisture absorption layer,
wherein the two or more adhesive layers and the moisture absorption layer exposure region are visible, as seen from the skin attachment surface.

2. The heat-generating device according to claim 1, wherein, on the surface of the moisture absorption layer, an area ratio of an adhesive layer formation region where the adhesive layer is formed relative to a moisture absorption layer exposure region where the moisture absorption layer is exposed is 100:5-2000.

3. The heat-generating device according to claim 1, wherein the packaging material constituting the skin attachment surface of the housing has a barrier function to block penetration of the warming agent.

4. The heat-generating device according to claim 3, wherein the moisture barrier layer contains a resin layer formed of polyethylene terephthalate, polyacrylonitrile, or an ethylene-vinyl alcohol copolymer; a vapor-deposited film; and/or a metal foil film.

5. The heat-generating device according to claim 1, wherein the moisture absorption layer is a fibrous sheet.

6. The heat-generating device according to claim 1, wherein the warming agent is contained in the adhesive layer.

7. The heat-generating device according to claim 1, wherein the warming agent is at least one selected from the group consisting of capsaicin, nonanoic acid vanillylamide, sage, caffeine, tocopherol nicotinate, nicotinic acid benzyl ester, vanillyl ethyl ether, vanillyl propyl ether, vanillyl butyl ether, vanillyl pentyl ether, vanillyl hexyl ether, vanillyl butyl ether acetate, gingerol, *Capsicum annuum* extract, and ginger extract.

8. The heat-generating device according to claim 1, wherein the heat-generating portion is an exothermic composition that generates heat upon contact with oxygen, and the housing is at least partially air-permeable.

9. The heat-generating device according to claim 1, wherein the moisture absorption layer exposure region is positioned just under the heat-generating portion.

10. The heat-generating device according to claim 1, wherein in the housing, the number of housing portion that contain the heat-generating portion is one.

* * * * *